United States Patent
Naasani

(10) Patent No.: US 10,610,591 B2
(45) Date of Patent: Apr. 7, 2020

(54) LIGHT RESPONSIVE QUANTUM DOT DRUG DELIVERY SYSTEM

(71) Applicant: Nanoco Technologies Ltd., Manchaster (GB)

(72) Inventor: Imad Naasani, Manchester (GB)

(73) Assignee: Nanoco Technologies Ltd., Manchester (GB)

( * ) Notice: Subject to any disclaimer, the term of this patent is extended or adjusted under 35 U.S.C. 154(b) by 0 days.

(21) Appl. No.: 15/913,606

(22) Filed: Mar. 6, 2018

(65) Prior Publication Data
US 2018/0264113 A1  Sep. 20, 2018

Related U.S. Application Data

(60) Provisional application No. 62/471,526, filed on Mar. 15, 2017.

(51) Int. Cl.
| | |
|---|---|
| *A61K 9/00* | (2006.01) |
| *A61K 41/00* | (2020.01) |
| *A61P 35/00* | (2006.01) |
| *A61K 31/00* | (2006.01) |
| *B82Y 5/00* | (2011.01) |
| *A61K 31/015* | (2006.01) |
| *A61K 47/68* | (2017.01) |
| *A61K 47/54* | (2017.01) |
| *A61K 47/69* | (2017.01) |
| *A61K 47/60* | (2017.01) |
| *A61K 47/52* | (2017.01) |
| *A61K 31/4745* | (2006.01) |
| *C07K 16/32* | (2006.01) |

(52) U.S. Cl.
CPC .......... *A61K 41/0042* (2013.01); *A61K 31/00* (2013.01); *A61K 31/015* (2013.01); *A61K 31/4745* (2013.01); *A61K 47/52* (2017.08); *A61K 47/542* (2017.08); *A61K 47/543* (2017.08); *A61K 47/545* (2017.08); *A61K 47/60* (2017.08); *A61K 47/6803* (2017.08); *A61K 47/6849* (2017.08); *A61K 47/6855* (2017.08); *A61K 47/6923* (2017.08); *A61K 47/6929* (2017.08); *A61P 35/00* (2018.01); *B82Y 5/00* (2013.01); *C07K 16/32* (2013.01); *C07K 2317/24* (2013.01)

(58) Field of Classification Search
CPC .................................................. A61K 41/0042
See application file for complete search history.

(56) References Cited

U.S. PATENT DOCUMENTS

| | | |
|---|---|---|
| 2005/0214380 A1 | 9/2005 | Bruch et al. |
| 2016/0022976 A1 | 1/2016 | Peyman |
| 2017/0209577 A1 | 6/2017 | Ambati et al. |

FOREIGN PATENT DOCUMENTS

| | | |
|---|---|---|
| WO | 2006099334 A2 | 9/2006 |
| WO | 2010008876 A2 | 1/2010 |

(Continued)

OTHER PUBLICATIONS

PCT Int'l Search Report received in copending PCT Application No. PCT/IB2018/051562 dated Jun. 5, 2018, 20 pages.

(Continued)

*Primary Examiner* — Paul W Dickinson
(74) *Attorney, Agent, or Firm* — Blank Rome, LLP

(57) ABSTRACT

Compositions and methods are described for delivery of drugs to desired tissues via soluble quantum dots.

25 Claims, 7 Drawing Sheets

(56) References Cited

FOREIGN PATENT DOCUMENTS

| WO | 2012173933 A2 | 12/2012 |
| WO | 2013093631 A2 | 6/2013 |

OTHER PUBLICATIONS

Hassan Niknejad et al: "Near-IR absorbing quantum dots might be usable for growth factor-based differentiation of stem cells", Journal of Medical Hypotheses and Ideas, vol. 9, No. 1, Mar. 1, 2015 (Mar. 1, 2015 ), pp. 24-28, XP055478417, ISSN: 2251-7294, DOI: 10.1016/j.jmhi.2015.01.003.

Lorenzo Sansalone et al: "Semiconductor Quantum Dots with Photoresponsive Ligands" In: "Photoactive Semiconductor Nanocrystal Quantum Dots", Oct. 28, 2016 (Oct. 28, 2016), Springer International Publishing, Cham, XP055478426, ISSN: 2367-4067 ISBN: 978-3-319-51192-4 pages 31-60, DOI: 10.1007/978-3-319-51192-4_2.

Ghaderi, Shirin et al.; "Fluorescence nanoparticles "quantum dots" as drug delivery system and their toxicity: a review"; Journal of Drug Targeting; 2011; 19(7); pp. 475-486.

Jeong, Da-Woon et al.; "One-pot synthesis of gradient interface quaternary ZnCdSSe quantum dots"; Applied Surface Science; 2016; pp. 1-5.

Liu, Dong et al.; "The Smart Drug Delivery System and Its Clinical Potential"; Theranostics; 2016; vol. 6; Issue 9; pp. 1306-1323.

Mura, Simona et al.; "Stimuli-responsive nanocarriers for drug delivery"; Nature Materials; vol. 12; Nov. 2013; pp. 991-1003.

Probst, Christine E. et al.; "Quantum dots as a platform for nanoparticle drug delivery vehicle design"; Advanced Drug Delivery Reviews; 65; 2013; pp. 703-718.

Qi, Lifeng et al.; "Emerging application of quantum dots for drug delivery and therapy"; Expert Opinion Drug Deliv.; 2008; 5(3); pp. 263-267.

Zhao, Mei-Xia et al.; "The Research and Applications of Quantum Dots as Nano-Carriers for Targeted Drug Delivery and Cancer Therapy"; Nanoscale Research Letters (2016) 11:2017; pp. 1-9.

Avdeef, Alex; "Absorption and Drug Development: Solubility, Permeability, and Charge State"; John Wiley & Sons, Inc.; pp. 1-307.

LIGHT RESPONSIVE QUANTUM DOT DRUG DELIVERY SYSTEM

FIELD OF THE INVENTION

This disclosure relates generally to compositions and methods for the delivery of drugs using quantum dot nanoparticles.

BACKGROUND OF THE INVENTION

Without limiting the scope of the invention, the background is described in connection with existing drug delivery systems. Stimuli-responsive drug delivery systems (DDS) are highly desirable if they can be engineered to deliver a drug in spatial-, temporal- and dosage-controlled manners. Specifically, the ability to trigger delivery is expected to enable time-controlled and targeted drug delivery and to reduce required dose, minimize systemic exposure and thus reduce overall toxicity. Several concepts have been proposed for stimuli-responsive DDS including protonation, hydrolytic cleavage and (supra)molecular conformational changes. Recent advances in the design of nanoscale stimuli-responsive systems are aimed to controlling drug biodistribution in response to specific stimuli including endogenous and exogenous stimuli. Proposed endogenous stimuli include changes in pH, enzyme concentration and redox gradients. Proposed exogenous stimuli include variations in temperature, magnetic field, ultrasound intensity, electric and light pulses. To date, light responsive drug therapy has focused on use of photosensitizing compounds and photoactive compounds that generate reactive oxygen species (ROS) upon light exposure. See, e.g. Liu, D., et al. "The Smart Drug Delivery System and Its Clinical Potential" *Theranostics* 6 (9) (2016) 1306-1323.

Existing approaches have not provided engineered light responsive molecules that respond to light with conformational changes. From the foregoing, it appears that compositions and methods are required that enable light induced drug delivery.

BRIEF SUMMARY OF THE INVENTION

In certain embodiments described herein, a light responsive quantum dot drug delivery system (QD-DDS) is provided that includes water soluble QD nanoparticles loaded with drug molecules, wherein the drug molecules are releasable from the QD-DDS upon light administration at a wavelength absorbed by the QD. In certain embodiments, the drug molecules are hydrophobic with an octanol-water partition coefficient (log P) of greater than 0. In certain embodiments the drug molecules are released upon excitation of the QDs with an excitation source selected from a normal blue light, UV light, laser light, LED light, multiphoton excitation, and an electrical current.

The water soluble QD nanoparticle in certain embodiments includes a core of one semiconductor material and at least one shell of a different semiconductor molecule in some embodiments while in other embodiments the water soluble QD nanoparticle includes an alloyed semiconductor material having a bandgap value that increases outwardly by graded alloying.

In certain embodiments the light responsive QD-DDS includes water soluble QD nanoparticles having a ligand interactive agent and a surface modifying ligand. The water soluble QD nanoparticle may be formed by chemical addition of the ligand interactive agent and the surface modifying ligand to the QD in a solution comprising hexamethoxymethylmelamine (HMMM). In particular embodiments the ligand interactive agent is a C8-20 fatty acid and esters thereof, while the surface modifying ligand is a monomethoxy polyethylene oxide.

In certain embodiments, the water soluble nanoparticles include capping ligands that are able to physically trap loaded drug molecules. In certain embodiments the capping ligand is selected from the group consisting of: thiol, carboxyl, amine, phosphine, phosphine oxide, phosphonic acid, phosphinic acid, imidazole, OH, thio ether, and calixarene groups.

In certain embodiments, the water soluble QD nanoparticle may be include a semiconductor material selected from the group of materials consisting of ZnS, ZnSe, ZnTe, InP, InAs, InSb, AlP, AlS, AlAs, AlSb, GaN, GaP, GaAs, GaSb, PbS, PbSe, AgInS$_2$, AgS, CuInS$_2$, Si, Ge and alloys and doped derivatives thereof. In other embodiments the water soluble QD includes a heavy metal semiconductor material selected from the group consisting of cadmium (Cd), lead (Pb), mercury (Hg), vanadium (V) and arsenic (As) and alloys and doped derivatives thereof.

The light responsive quantum dot (QD) drug delivery system may include QD that are derivatized with a targeting ligand prior to loading with the drug. In certain embodiments the targeting ligand is a monoclonal antibody directed to a target selected from the group consisting of: carcinoembryonic antigen (CEA), epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumour necrosis factor (TNF)-related apoptosis-inducing ligand receptor 1 (TRAILR1; also known as TNFRSF10A), TRAILR2 (also known as TNFRSF10B), receptor activator of nuclear factor-KB ligand (RANKL; also known as TNFSF11), VEGF receptor (VEGFR), integrin $\alpha V\beta 3$, integrin $\alpha 5\beta 1$, fibroblast activation protein (FAP), tenascin, CD20, CD30, CD33, CD52, EpCAM, gpA33, Mucins, TAG-72, carbonic anhydrase IX (CAIX), PSMA, folate-binding protein, gangliosides GD2, GD3 and GM2, PD-L2, and telomerase subunits.

Methods of treating a target tissue are provided including administering a drug loaded light responsive QD drug delivery system and administering light to the target tissue sufficient to induce release of the drug from the drug delivery system at a desired time and place for purposes of diagnosing, treating, curing, mitigating, or preventing disease states of humans, animals, plants, and other organisms.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

Figure 1:
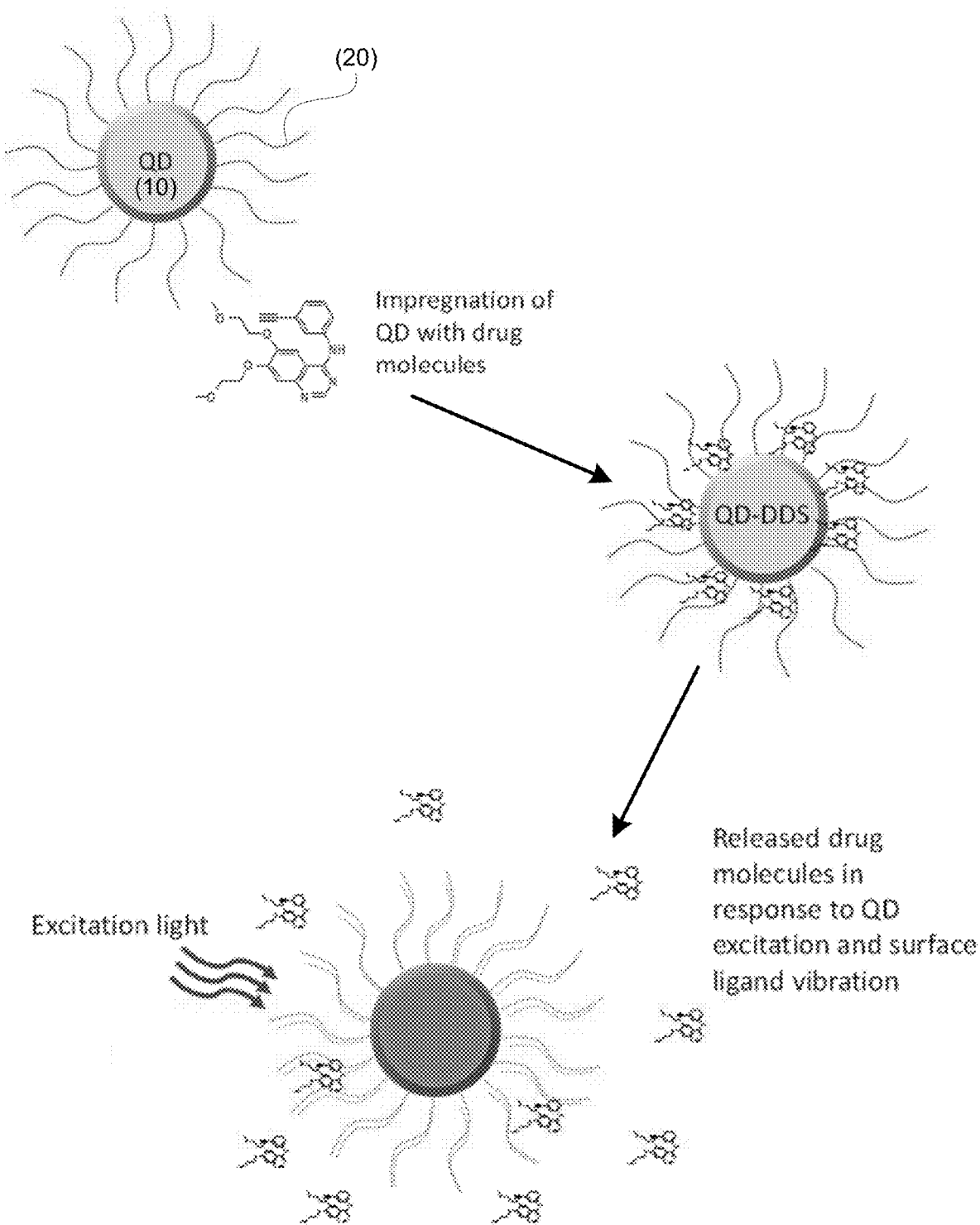
FIG. 1 provides a schematic of drug loading of quantum dots and release of the drug with light excitation.

Appreciating the shortcomings of existing technologies, the present inventors undertook to provide drug delivery QD that are able to be loaded with drugs and have the ability to release the loaded drugs upon stimulation. Provided herein are certain embodiments that provide QDs that feature high safety and biocompatibility profiles and are loadable with drugs that are released from the QD upon irradiation. In certain embodiments, the delivery device is engineered as a conjugate of biocompatible, non-toxic, fluorescent QDs with a drug. In other embodiment, the drug delivering QD include cytotoxic drugs and are formed of semiconductor materials that are themselves toxic and contribute to the cytotoxicity of the drug delivery system. In other embodiments, the delivery device is engineered as a simple QDs with passivating ligands or coating that allows the adsorption of drug molecules.

QDs are fluorescent semiconductor nanoparticles with superb optical properties. They shine around 20 times brighter and are many times more photo-stable than any of the conventional fluorescent dyes (like indocyanine green (ICG)). Importantly, QD residence times are longer due to their chemical nature and nano-size. QDs can absorb and emit much stronger light intensities. In certain embodiments, the drug loaded QD can be equipped with more than one binding tag, forming bi- or tri-specific nano-devices. The unique properties of QDs enable several medical applications that serve unmet needs targeted drug delivery and photodynamic therapy. Such conjugates are thus "theranostic" nano-devices with multimodal properties including the ability to locate delivered drugs and to provide a time-controlled and focal treatment of disease.

As used herein the term "drug" includes any medicinal compound including both hydrophobic and hydrophilic drugs. While certain drugs can be delivered by enteral administration, other drugs are typically delivered parenterally. Enteral delivery can be sublingual, orally or rectally. Parenteral delivery can be by venous, arterial, thecal, intramuscular or subcutaneous injection as well as by inhalation and topical delivery. Once absorbed into the bloodstream, drugs rapidly circulate through the body with an average circulation time 1 minute. As the blood recirculates, the drug moves from the bloodstream into tissues. Water-soluble (hydrophilic) drugs tend to stay within the blood and extracellular fluids while fat soluble (hydrophobic) drugs tend to concentrate in fatty tissues.

Hydrophobic drugs are poorly water soluble if at all and pose a challenge for drug delivery, particularly by oral routes. Oral delivery is the most convenient and commonly employed drug delivery route due to ease of administration and patient compliance, cost effectiveness, least sterility concerns, and flexibility of dosage form. By one estimate, approximately 40% drugs with market approval and 90% of drugs in the delivery pipeline are poorly or practically insoluble in water. Such drugs when delivered orally have slow drug absorption with inadequate and variable bioavailability and gastrointestinal mucosal toxicity. Consequently, solubility is a critical rate limiting parameter for orally administered drugs to achieve desired concentrations in systemic circulation. In order to improve the bioavailability of water insoluble drugs, typical approaches include physically and/or chemically modified the drug including by particle size reduction, crystal engineering, and salt formation. Examples of poorly water soluble drugs that have been subject to micro or nanonization include immunosuppressive drugs such as rapamycin (a.k.a. sirolimus), anticancer drugs such as paclitaxel, cholesterol reducing drugs including fenofibrate, and hormones such as danazol.

The water insoluble drug may require formulation with a surfactant or co-solvent that may cause adverse reactions in the patient. Examples of poorly soluble drugs that are formulated with co-solvents and surfactants include anti-cancer drugs such as paclitaxel and teniposide, immunosuppressive drugs such as tacrolimus, vasoconstrictive drugs such as dihydroergotamine, anti-infectives such as doxycyclin, and muscle relaxants such as methocarbamil. In other cases the water insoluble drug may be formed as a solid dispersion with a carrier molecule. Examples of marketed poorly or insoluble drugs formulated as solid dispersions include anti-infectives such as itraconazole (Sporanox®), immunosuppressive drugs such as tacrolimus (Prograf®), antivirals such as lopinavir/ritonavir (Kaletra®) and etravirine (Intelence®), and cholesterol reducing drugs such as fenofibrate (Fenoglide®). Certain insoluble drugs are subject to inclusion complexation with a host coating molecule such as a cyclodextran. In other cases the water insoluble drug is formulated as micelles or in liposomes. Examples of micellular formulations both marketed and under development include anti-cancer drugs such as paclitaxel, doxorubicin, SN-38 (7-Ethyl-10-hydroxycamptothecin), cisplatin, oxaliplatin, epirubicin, and DACH-platin (metabolite of oxaliplatin). Estrogens such as estradiol are formulated as micellar nanoparticles for transdermal delivery. Because insulin is poorly soluble at neutral pH, formulations for oral delivery are being developed using micellar formulations. Examples of water insoluble drugs delivered in liposomes anti-infectives such as amphotericin B, amikacin and nystatin, and anti-neoplastics such as daunorubicin citrate, tretinoin, doxorubicin and vincristine. The poorly water soluble drug may be formulated into a solid lipid nanoparticle (SLN). Examples of drug formulated with SLN technology include pain control drugs such as apomorphine, immunosuppressive drugs such as cyclosporin A, hormones such as gonadotropin release hormone, progesterone and insulin, anti-inflammatories such as ibuprofen and nimusulide, anti-neoplastics drugs such as idarubicin and 5-fluoro uracil, anti-infectives such as lopinavir and tetracycline, and anti-hyperglycemic agents such as repaglinide.

Insoluble or poorly soluble drugs that are hydrophobic as the basis of insolubility may be delivered by loading on QD as disclosed herein. In one embodiment, the drug loaded QD is delivered directly or the local environment of the target tissue. A light source is then placed in proximity to the target tissue and light is delivered sufficient to induce release of the drug from the QD with increased local concentrations. Many of the above listed drugs have considerable and dose limiting systemic toxicity that can be avoided by the local release disclosed herein. In one embodiment a solution is provided to systemic drug toxicity wherein the hydrophobic drug is loaded onto QD and administered to the patient. The drug is released by administering light into the local environment of the target tissue either by open or closed procedures. Thus, the drug can be delivered by local release in concentrations that could not be safely administered systemically.

In embodiments presented herein, the QDs are functionalized to present a hydrophilic outer layer or corona that permits use of the QDs in the aqueous environment of the body. Such QDs are termed water soluble QDs. In certain embodiments the water soluble QD is loaded with water soluble drugs. Because release of the drug is performed with light administration, a water soluble drug can administered and remain associated with the QD until release is desired. For one example, a water soluble QD loaded with a water soluble drug can be administered by mouth and remain in association with the QD until it arrives at a desired location in the alimentary tract without entering the circulation by immediate absorption such as in the mouth.

For one example of delivery systemically in the treatment of tumors, the drug loaded QD, whether the drug is hydrophobic or hydrophilic, is administered parenterally and allowed to circulate until the drug loaded QD has concentrated in the tumor. Particulates such as QDs are expected to accumulate in the vasculature of tumors after repeated passes through the circulation because the spongey vasculature of tumors is known to trap particulates in circulation to levels higher than those existing systemically. This phenomenon is known as Enhanced Permeability and Retention effect (EPR). In one embodiment the QD includes polyethylene glycol (PEG) moieties that reduce removal of the QD by the reticuloendothelial system as they circulate such that the QD is allowed to accumulate in the tumor. Once the QDs are delivered to the tumor, the loaded drug is released by administering light into the local environment of the target tissue either by open or closed procedures. In one embodiment of light administered into the local environment of the tumor, the tumor is a neuroendocrine intra-abdominal tumor and the light source is introduced into the abdomen endoscopically. In other embodiments, the drug loaded QD is injected directly into the tumor tissue and drug is released by administering light into the local environment of the target tumor either by open or closed procedures.

In one embodiment the QD for drug loading may be surface equipped with a conjugation capable function (COOH, OH, $NH_2$, SH, azide, alkyne). In one exemplified embodiment, the water soluble non-toxic QD is or becomes carboxyl functionalized. For targeted drug delivery indications, the COOH-QD may be linked to the amine terminus of a targeting antibody using a carbodiimide linking technology employing water-soluble 1-ethyl-3-(-3-dimethylaminopropyl) carbodiimide hydrochloride (EDC). The carboxyl functionalized QD is mixed with EDC to form an active O-acylisourea intermediate that is then displaced by nucleophilic attack from primary amino groups on the monoclonal antibody in the reaction mixture. If desired, a sulfo derivative of N-hydroxysuccinimide (sulfo-NHS) is added during the reaction with the primary amine bearing antibody. With the sulfo-NHS addition, the EDC couples NHS to carboxyls, forming an NHS ester that is more stable than the O-acylisourea intermediate while allowing for efficient conjugation to primary amines at physiologic pH. In either event, the result is a covalent bond between the QD and the antibody. Other chemistries like Suzuki-Miyaura cross-coupling, (succinimidyl 4-(N-maleimidomethyl)cyclohexane-1-carboxylate) (SMCC), or aldehyde based reactions may alternatively be used.

Methods of synthesizing core and core-shell nanoparticles are disclosed, for example, in co-owned U.S. Pat. Nos. 7,867,556, 7,867,557, 7,803,423, 7,588,828, and 6,379,635. The contents of each of the forgoing patents are hereby incorporated by reference, in their entirety. U.S. Pat. Nos. 9,115,097, 8,062,703, 7,985,446, 7,803,423, and 7,588,828, and U.S. Publication Nos. 2010/0283005, 2014/0264196, 2014/0277297 and 2014/0370690, the entire contents of each of which are hereby incorporated by reference, describe methods of producing large volumes of high quality monodisperse quantum dots.

In certain embodiments, the light responsive QD-DDS utilizes a water soluble QD nanoparticle that is considered a "core only" nanoparticle formed of a semiconductor material but lacking an inorganic shell of a different semiconductor material. Core only QDs are capable of light absorption but in some cases do not exert strong fluorescence emission and thus have been disfavored for purposes where light emission is the purpose of the QD. When used for drug delivery, core only QDs that lack strong fluorescence emission but have sufficient energy absorption for structural perturbation and drug release upon light excitation may be utilized.

In other embodiments a core/shell particle is utilized having a central region or "core" of at least one semiconductor composition buried in or coated by one or more outer layers or "shell" of distinctly different semiconductor compositions. As an example, the core may be comprised of an alloy of In, P, Zn and S such as is formed by the description of Example 1 involving molecular seeding of InP over a ZnS molecular cluster followed by formation of a shell of ZnS.

In still other embodiments, the water soluble QD nanoparticle employed comprises an alloyed semiconductor material having a bandgap value or energy ($E_g$) that increases outwardly by graded alloying in lieu of production of a core/shell QD. The band gap energy ($E_g$), is the minimum energy required to excite an electron from the ground state valence energy band into the vacant conduction energy band.

The graded alloy QD composition is considered "graded" in elemental composition from at or near the centre of the particle to the outermost surface of the QD rather than formed as a discrete core overlaid by a discrete shell layer. An example would be an $In_{1-x}P_{1-y}Zn_xS_y$ graded alloy QD wherein the x and y increase gradually from 0 to 1 from the centre of the QD to the surface. In such example, the band gap of the QD would gradually change from that of pure InP towards the centre to that of a larger band gap value of pure ZnS at the surface. Although the band gap is dependent on particle size, the band gap of ZnS is wider than that of InP such that the band gap of the graded alloy would gradually increase from an inner aspect of the QD to the surface.

A one-pot synthesis process may be employed as a modification of the molecular seeding process described in Example 1 herein. This may be achieved by gradually decreasing the amounts of indium myristate ($In(MA)_3$) and $(TMS)_3P$ added to the reaction solution to maintain particle growth, while adding increasing amounts of zinc and sulfur precursors during a process such as is described for generation of the "core" particle of Example 1. Thus, in one example a dibutyl ester and a saturated fatty acid are placed into a reaction flask and degassed with heating. Nitrogen is introduced and the temperature is increased. A molecular cluster, such as for example a ZnS molecular cluster $[Et_3NH]_4[Zn_{10}S_4(SPh)_{16}]$, is added with stirring. The temperature is increased as graded alloy precursor solutions are added according to a ramping protocol that involves addition of gradually decreasing concentrations of a first semiconductor material and gradually increasing concentrations of a second semiconductor material. For example, the ramping protocol may begin with additions of $In(MA)_3$ and trimethylsilyl phosphine $(TMS)_3P$ dissolved in a dicarboxylic acid ester (such as for example di-n-butylsebacate ester) wherein the amounts of added $In(MA)_3$ and $(TMS)_3P$ gradually decrease over time to be replaced with gradually increasing concentration of sulfur and zinc compounds such as $(TMS)_2S$ and zinc acetate. As the added amounts of $In(MA)_3$ and $(TMS)_3P$ decrease, gradually increasing amounts of $(TMS)_2S$ dissolved in a saturated fatty acid (such as for example myristic or oleic acid) and a dicarboxylic acid ester (such as di-n-butyl sebacate ester) are added together with the zinc acetate. The following reactions will result in the increasing generation of ZnS compounds. As the additions continue, QD particles of a desired size with an emission maximum gradually increasing in wavelength are formed wherein the concentrations of InP and ZnS are graded with the highest concentrations of InP towards a center of the QD particle and the highest concentrations of ZnS on an outer of the QD particle. Further additions to the reaction are stopped when the desired emission maximum is obtained and the resultant graded alloy particles are left to anneal followed by isolation of the particles by precipitation and washing.

A nanoparticle's compatibility with a medium as well as the nanoparticle's susceptibility to agglomeration, photo-oxidation and/or quenching, is mediated largely by the surface composition of the nanoparticle. The coordination about the final inorganic surface atoms in any core, core-shell or core-multi shell nanoparticle may be incomplete, with highly reactive "dangling bonds" on the surface, which can lead to particle agglomeration. This problem is overcome by passivating (capping) the "bare" surface atoms with protecting organic groups, referred to herein as capping ligands or a capping agent. The capping or passivating of particles prevents particle agglomeration from occurring but also protects the particle from its surrounding chemical environment and provides electronic stabilization (passivation) to the particles, in the case of core material. Capping ligands may be but are not limited to a Lewis base bound to surface metal atoms of the outer most inorganic layer of the particle. The nature of the capping ligand largely determines the compatibility of the nanoparticle with a particular medium. In certain embodiments disclosed herein, capping ligands are selected for the purpose of physically trapping drug molecules to be loaded onto the QD. Capping ligand may be selected depending on desired characteristics. Types of capping ligands that may be employed include thiol groups, carboxyl, amine, phosphine, phosphine oxide, phosphonic acid, phosphinic acid, imidazole, OH, thio ether, and calixarene groups. With the exception of calixarenes, all of these capping ligands have head groups that can form anchoring centers for the capping ligands on the surface of the particle. The body of the capping ligand can be a linear chain, cyclic, or aromatic. The capping ligand itself can be large, small, oligomeric or polydentate. The nature of the body of the ligand and the protruding side that is not bound onto the particle, together determine if the ligand is hydrophilic, hydrophobic, amphiphilic, negative, positive or zwitterionic.

In many quantum dot materials, the capping ligands are hydrophobic (for example, alkyl thiols, fatty acids, alkyl phosphines, alkyl phosphine oxides, and the like). Thus, the nanoparticles are typically dispersed in hydrophobic solvents, such as toluene, following synthesis and isolation of the nanoparticles. Such capped nanoparticles are typically not dispersible in more polar media. If surface modification of the QD is desired, the most widely used procedure is known as ligand exchange. Lipophilic ligand molecules that coordinate to the surface of the nanoparticle during core synthesis and/or shelling procedures may subsequently be exchanged with a polar/charged ligand compound. An alternative surface modification strategy intercalates polar/charged molecules or polymer molecules with the ligand molecules that are already coordinated to the surface of the nanoparticle. However, while certain ligand exchange and intercalation procedures render the nanoparticle more compatible with aqueous media, they may result in materials of lower quantum yield (QY) and/or substantially larger size than the corresponding unmodified nanoparticle.

For in vivo purposes, QDs with low toxicity profiles are desirable if not required. Thus, for some theranostic purposes, the QD is preferably substantially free of toxic heavy metals such as cadmium, lead and arsenic (e.g., contains less than 5 wt. %, such as less than 4 wt. %, less than 3 wt. %, less than 2 wt. %, less than 1 wt. %, less than 0.5 wt. %, less than 0.1 wt. %, less than 0.05 wt. %, or less than 0.01 wt. % of heavy metals such as cadmium, lead and arsenic) or is free of heavy metals such as cadmium, lead and arsenic. In one embodiment, reduced toxicity QD that lack heavy metals such as cadmium and lead are provided for use in drug loading. On the other hand, in some embodiments such as where a toxic drug is being delivered, it may be desirable to have the QD itself confer further toxicity. In such cases QD formed of heavy metals such as toxic heavy metals such as cadmium, lead and arsenic may be employed.

The unique properties of QDs enable several potential medical applications including unmet in vitro and in vivo diagnostics, clinical imaging, targeted drug delivery, and photodynamic therapy. One of the major concerns regarding the medical applications of QDs has been that the majority of research has focused on QDs containing toxic heavy metals such as cadmium, lead or arsenic. The biologically compatible and water-soluble heavy metal-free QDs described herein can safely be used in medical applications both in vitro and in vivo. In certain embodiments, in vivo compatible water dispersible cadmium-free QDs are provided that have a hydrodynamic size of 10-20 nm (within the range of the dimensional size of a full IgG2 antibody). In one embodiment, the in vivo compatible water dispersible cadmium-free QDs are produced in accordance with the procedures set out in Examples 1 and 2 herein. In certain embodiments, the in vivo compatible water dispersible cadmium-free QDs are carboxyl functionalized and further derivatized with a ligand binding moiety.

In vitro and in vivo toxicology studies with the in vivo compatible water dispersible cadmium-free QDs disclosed herein showed them to be are at least 20 times less cytotoxic than commercially available cadmium-based QDs, and no toxicity signs were observed on animal models at multiple times higher than useful doses. Furthermore, the in vivo compatible water dispersible cadmium-free QD nanoparticles herein provided showed no hemolytic effect and no complement C3 activation, indicating a favorable clinical compatibility profile.

Examples of cadmium, lead and arsenic free nanoparticles include nanoparticles comprising semiconductor materials, e.g., ZnS, ZnSe, ZnTe, InP, InSb, AlP, AlS, AlSb, GaN, GaP, GaSb, PbS, PbSe, $AgInS_2$, $CuInS_2$, Si, Ge, and alloys and doped derivatives thereof, particularly, nanoparticles comprising cores of one of these materials and one or more shells of another of these materials.

It is noted that nanoparticles that include a single semiconductor material, e.g., CdS, CdSe, ZnS, ZnSe, InP, GaN, etc. may have relatively low quantum efficiencies because of non-radiative electron-hole recombination that occurs at defects and dangling bonds at the surface of the nanoparticles. In order to at least partially address these issues, the nanoparticle cores may be at least partially coated with one or more layers (also referred to herein as "shells") of a material different than that of the core, for example a different semiconductor material than that of the "core." The material included in the one or more shells may incorporate ions from any one or more of groups 2 to 16 of the periodic table. When a nanoparticle has two or more shells, each shell may be formed of a different material. In an exemplary core/shell material, the core is formed from one of the materials specified above and the shell includes a semiconductor material of larger band-gap energy and similar lattice dimensions as the core material. Exemplary shell materials include, but are not limited to, ZnS, ZnO, ZnSe, MgS, MgSe, MgTe and GaN. One example of a multi-shell nanoparticle is InP/ZnS/ZnO. The confinement of charge carriers within the core and away from surface states provides nanoparticles of greater stability and higher quantum yield.

However, while it may be desirable to have QDs that lack toxic heavy metals, it has proved particularly difficult to modify the surface of cadmium-free nanoparticles. Cadmium-free nanoparticles readily degrade when methods such as the aforementioned ligand exchange methods are used to modify the surface of such cadmium-free nanoparticles. For example, attempts to modify the surface of cadmium-free nanoparticles have been observed to cause a significant decrease in the luminescence QY of such nanoparticles. For certain in vivo purposes disclosed herein, surface-modified cadmium-free nanoparticles with high QY are required. The high QY cadmium-free water dispersible nanoparticles disclosed herein have a QY greater than about 20%, greater than about 25%, greater than about 30%, greater than about 35%, or greater than about 40%. For certain in vivo embodiments, heavy metal-free semiconductor indium-based nanoparticles or nanoparticles containing indium and/or phosphorus are preferred.

In certain embodiments, non-toxic QD nanoparticles are surface modified to enable them to be water soluble and to have surface moieties that allow derivatization by exposing them to a ligand interactive agent to effect the association of the ligand interactive agent and the surface of the QD. The ligand interactive agent can comprise a chain portion and a functional group having a specific affinity for, or reactivity with, a linking/crosslinking agent, as described below. The chain portion may be, for example, an alkane chain. Examples of functional groups include nucleophiles such as thio groups, hydroxyl groups, carboxamide groups, ester groups, and a carboxyl groups. The ligand interactive agent may, or may not, also comprise a moiety having an affinity for the surface of a QD. Examples of such moieties include thiols, amines, carboxylic groups, and phosphines. If ligand interactive group does not comprise such a moiety, the ligand interactive group can associate with the surface of nanoparticle by intercalating with capping ligands. Examples of ligand interactive agents include $C_{8-20}$ fatty acids and esters thereof, such as for example isopropyl myristate.

It should be noted that the ligand interactive agent may be associated with QD nanoparticle simply as a result of the processes used for the synthesis of the nanoparticle, obviating the need to expose nanoparticle to additional amounts of ligand interactive agents. In such case, there may be no need to associate further ligand interactive agents with the nanoparticle. Alternatively, or in addition, QD nanoparticle may be exposed to ligand interactive agent after the nanoparticle is synthesized and isolated. For example, the nanoparticle may be incubated in a solution containing the ligand interactive agent for a period of time. Such incubation, or a portion of the incubation period, may be at an elevated temperature to facilitate association of the ligand interactive agent with the surface of the nanoparticle. Following association of the ligand interactive agent with the surface of nanoparticle, the QD nanoparticle is exposed to a linking/crosslinking agent and a surface modifying ligand. The linking/crosslinking agent includes functional groups having specific affinity for groups of the ligand interactive agent and with the surface modifying ligand. The ligand interactive agent-nanoparticle association complex can be exposed to linking/crosslinking agent and surface modifying ligand sequentially. For example, the nanoparticle might be exposed to the linking/crosslinking agent for a period of time to effect crosslinking, and then subsequently exposed to the surface modifying ligand to incorporate it into the ligand shell of the nanoparticle. Alternatively, the nanoparticle may be exposed to a mixture of the linking/crosslinking agent and the surface modifying ligand thus effecting crosslinking and incorporating surface modifying ligand in a single step.

The following examples are include for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Synthesis of Non-Toxic Quantum Dots

A molecular seeding process was used to generate non-toxic QDs. Briefly, the preparation of non-functionalized indium-based quantum dots with emission in the range of 500-700 nm was carried out as follows: Dibutyl ester (approximately 100 ml) and myristic acid (MA) (10.06 g) were placed in a three-neck flask and degassed at ~70° C. under vacuum for 1 h. After this period, nitrogen was introduced and the temperature was increased to ~90° C. Approximately 4.7 g of a ZnS molecular cluster $[Et_3NH]_4$ $[Zn_{10}S_4(SPh)_{16}]$ was added, and the mixture was stirred for approximately 45 min. The temperature was then increased to ~100° C., followed by the drop-wise additions of $In(MA)_3$ (1M, 15 ml) followed by trimethylsilyl phosphine $(TMS)_3P$ (1M, 15 ml). The reaction mixture was stirred while the temperature was increased to ~140° C. At 140° C., further drop-wise additions of $In(MA)_3$ dissolved in di-n-butylsebacate ester (1M, 35 ml) (left to stir for 5 min) and $(TMS)_3P$ dissolved in di-n-butylsebacate ester (1M, 35 ml) were made. The temperature was then slowly increased to 180° C., and further dropwise additions of $In(MA)_3$ (1M, 55 ml) followed by $(TMS)_3P$ (1M, 40 ml) were made. By addition of the precursor in this manner, indium-based particles with an emission maximum gradually increasing from 500 nm to 720 nm were formed. The reaction was stopped when the desired emission maximum was obtained and left to stir at the reaction temperature for half an hour. After this period, the mixture was left to anneal for up to approximately 4 days (at a temperature ~20-40° C. below that of the reaction). A UV lamp was also used at this stage to aid in annealing.

The particles were isolated by the addition of dried degassed methanol (approximately 200 ml) via cannula techniques. The precipitate was allowed to settle and then methanol was removed via cannula with the aid of a filter stick. Dried degassed chloroform (approximately 10 ml) was added to wash the solid. The solid was left to dry under vacuum for 1 day. This procedure resulted in the formation of indium-based nanoparticles on ZnS molecular clusters. In further treatments, the quantum yields of the resulting indium-based nanoparticles were further increased by washing in dilute hydrofluoric acid (HF). The quantum efficiencies of the indium-based core material ranged from approximately 25%-50%. This composition is considered an alloy structure comprising In, P, Zn and S.

Growth of a ZnS shell: A 20 ml portion of the HF-etched indium-based core particles was dried in a three-neck flask. 1.3 g of myristic acid and 20 ml di-n-butyl sebacate ester were added and degassed for 30 min. The solution was heated to 200° C., and 2 ml of 1 M $(TMS)_2S$ was added drop-wise (at a rate of 7.93 ml/h). After this addition was complete, the solution was left to stand for 2 min, and then 1.2 g of anhydrous zinc acetate was added. The solution was kept at 200° C. for 1 hr. and then cooled to room temperature. The resulting particles were isolated by adding 40 ml of anhydrous degassed methanol and centrifuging. The supernatant liquid was discarded, and 30 ml of anhydrous degassed hexane was added to the remaining solid. The solution was allowed to settle for 5 h and then centrifuged again. The supernatant liquid was collected and the remaining solid was discarded. The QYs of the final non-functionalized indium-based nanoparticle material ranged from approximately 60%-90% in organic solvents.

EXAMPLE 2

Water Soluble Surface Modified QDs

Provided herein is one embodiment of a method for generating and using melamine hexamethoxymethyl-melamine (HMMM) modified fluorescent nanoparticles as drug delivery vehicles. The unique melamine-based coating presents excellent biocompatibility, low toxicity and very low non-specific binding. These unique features allow a wide range of biomedical applications both in vitro and in vivo.

One example of preparation of a suitable water soluble nanoparticle is provided as follows: 200 mg of cadmium-free QDs with red emission at 608 nm having as a core material an alloy comprising indium and phosphorus with Zn-containing shells as described in Example 1 was dispersed in toluene (1 ml) with isopropyl myristate (100 microliters). The isopropyl myristate is included as the ligand interactive agent. The mixture was heated at 50° C. for about 1-2 minutes then slowly shaken for 15 hours at room temperature. A toluene solution (4 ml) of HMMM (CYMEL 303, available from Cytec Industries, Inc., West Paterson, N.J.) (400 mg), monomethoxy polyethylene oxide ($CH_3O$-$PEG_{2000}$-OH) (400 mg), and salicylic acid (50 mg) was added to the nanoparticle dispersion. The salicylic acid that is included in the functionalization reaction plays three roles, as a catalyst, a crosslinker, and a source for COOH. Due in part to the preference of HMMM for OH groups, many COOH groups provided by the salicylic acid remain available on the QD after crosslinking.

HMMM is a melamine-based linking/crosslinking agent having the following structure:

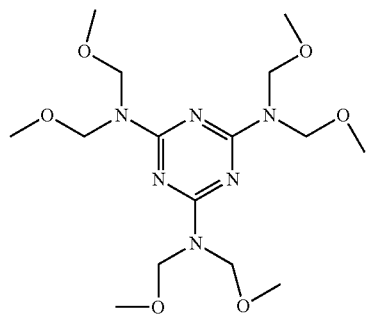

HMMM can react in an acid-catalyzed reaction to cross-link various functional groups, such as amides, carboxyl groups, hydroxyl groups, and thiols.

The mixture was degassed and refluxed at 130° C. for the first hour followed by 140° C. for 3 hours while stirring at 300 rpm with a magnetic stirrer. During the first hour a stream of nitrogen was passed through the flask to ensure the removal of volatile byproducts generated by the reaction of HMMM with nucleophiles. The mixture was allowed to cool to room temperature and stored under inert gas. The surface-modified nanoparticles showed little or no loss in fluorescence quantum yield and no change in the emission peak or full width at half maximum (FWHM) value, compared to unmodified nanoparticles. An aliquot of the surface-modified nanoparticles was dried under vacuum and deionized water was added to the residue. The surface-modified nanoparticles dispersed well in the aqueous media and remained dispersed permanently. In contrast, unmodified nanoparticles could not be suspended in the aqueous medium. The fluorescence QY of the surface-modified nanoparticles according to the above procedure is 40-50%. In typical batches, a quantum yield of 47%±5% is obtained.

In another embodiment, cadmium-free QDs (200 mg) with red emission at 608 nm were dispersed in toluene (1 ml) with cholesterol (71.5 mg) included as the ligand interactive agent. The mixture was heated at 50° C. for about 1-2 minutes then slowly shaken for 15 hours at room temperature. A toluene solution (4 ml) of HMMM (Cymel 303) (400 mg), monomethoxy polyethylene oxide ($CH3O$-$PEG2000$-OH) (400 mg), guaifenesin (100 mg), dichloromethane (DCM) (2 mL) and salicylic acid (50 mg) was added to the nanoparticle dispersion.

As used herein the compound "guaifenesin" has the following chemical structure:

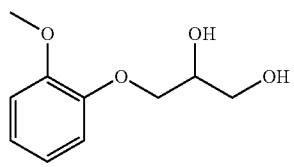

As used herein the compound "salicylic acid" has the following chemical structure:

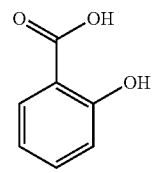

Figure 2:
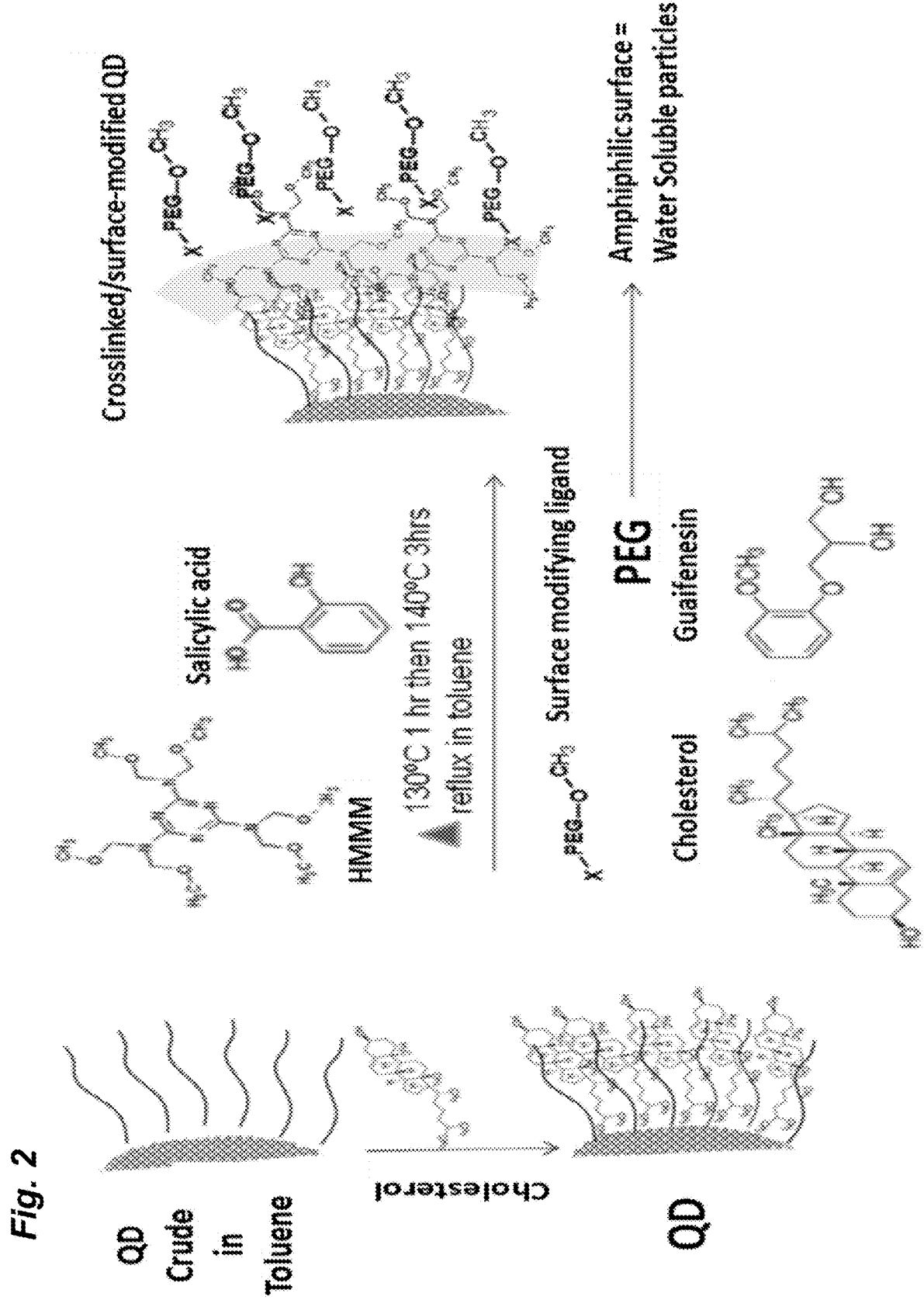
FIG. 2 depicts one embodiment of generation of water soluble quantum dots.

The mixture was degassed and refluxed at 140° C. for 4 hours while stirring at 300 rpm with a magnetic stirrer. As with the prior procedure, during the first hour a stream of nitrogen was passed through the flask to ensure the removal of volatile byproducts generated by the reaction of HMMM with nucleophiles. The mixture was allowed to cool to room temperature and stored under inert gas. An aliquot of the surface-modified nanoparticles was dried under vacuum and deionized water was added to the residue. The pH of the solution was adjusted to 6.5 using a 100 mM KOH solution and the excess non reacted material was removed by three cycles of ultrafiltration using Amicon filters (30 kD). The final aqueous solution was kept refrigerated until use. FIG. 2 depicts a generation process and resulting surface modified QD.

It is noteworthy that traditional methods for modifying nanoparticles to increase their water solubility (e.g., ligand exchange with mercapto-functionalized water soluble ligands) are ineffective under mild conditions to render the nanoparticles water soluble. Under harsher conditions, such as heat and sonication, the fraction that becomes water soluble has very low QY (<20%). The instant method, in contrast, provides water soluble nanoparticles with high quantum yield. As defined herein, a high quantum yield is equal to or greater than 40%. In certain embodiments, a high quantum yield is obtained of equal to or greater than 45%. The surface-modified nanoparticles prepared as in this example also disperse well and remain permanently dispersed in other polar solvents, including ethanol, propanol, acetone, methylethylketone, butanol, tripropylmethylmethacrylate, or methylmethacrylate.

EXAMPLE 3

Light Responsive Drug Delivery System

In one embodiment, non-toxic water soluble QDs are generated, including according to Examples 1 and 2, and are subsequently loaded with a drug. In other embodiments, the QDs include heavy metal semiconductor materials such as cadmium, lead and arsenic. Examples of such materials include lead sulfide (PbS), lead selenide (PbSe), cadmium selenide (CdSe), cadmium sulfide (CdS), cadmium telluride (CdTe), cadmium selenide sulfide (CdSeS), gallium arsenide (GdAs), indium arsenide (InAs) and hybrids and alloys thereof such as for non-limiting example $CdSe_{1-x}Te_x$ ($0 \leq x \leq 1$) and $Cd_{1-x}Zn_xSe_{1-y}Te_y$ ($0 \leq x$; $y \leq 1$). In some embodiments, where the drug delivery system is used to deliver a drug that controls cell proliferation or results in cell death, use of QDs including toxic heavy metals provides that the QD drug carrier itself contributes to the cytotoxicity of the combined system through its inherent toxicity. One such example is use in tumorocidal applications. In other embodiments, the indication is in treatment of a non-malignant hyperproliferative disorder such as psoriasis and the drug delivery system is administered topically. In certain embodiments such as for example for use in treatment of psoriasis, the QD of the drug delivery system may include cadmium or arsenates that contribute to apoptosis of cells to which they are administered. Liberation of cytotoxic atoms such as the Cd' atoms from CdSe quantum dots may be accomplished by several mechanisms including oxidation and ultraviolet irradiation. See Derfus, A M, et al. "Probing the Cytotoxicity of Semiconductor Quantum Dots" *Nano Letters* 4 (1) (2004) 11-18.

In certain embodiments the drug is a hydrophobic drug molecule loaded on the QD by first dissolving the drug in a solvent with dual miscibility in water and oil (e.g., dimethyl sulfoxide (DMSO), alcohols, propylene glycol, tetrahydrofuran (THF), etc.). The drug solution is then added drop wise to an aqueous solution of QDs. The drug may be added in an amount that does not overly exceed the loading capacity of the QDs as can be determined by visual and other types of inspection. Excess unbound drug molecules can be removed by ultrafiltration or dialysis. When loading hydrophobic drugs, the hydrophobicity of the drug is high enough to force the drug molecules to migrate directly from their solvent into the surface of the QD without long residence in the aqueous media. In certain embodiments, the QD is modified to match the hydrophobicity and Hansen solubility parameters of the drug. In certain embodiments, the drug molecules are hydrophobic with an octanol-water partition coefficient (log P) of greater than 0. (Log P=0 is when hydrophilicity=hydrophobicity. A log P greater than 0 is hydrophobic, and while a value less than 0 is hydrophilic.) In other embodiments, the drug molecules are hydrophobic with an octanol-water partition coefficient (log P) of greater than 1. (A log P of 1 would mean a 10:1 distribution of the drug in the organic phase.)

A partition-coefficient (P) or distribution-coefficient (D) is the ratio of concentrations of a compound in a mixture of two immiscible phases at equilibrium and constitutes a measure of the solubility difference of the compound in the two phases. The partition-coefficient is the most widely used measure of the hydrophobicity/hydrophilicity of a compound. The partition coefficient is expressed as the log P or log $P_{exp}$. Where calculated rather than determined experimentally the partition coefficient is called the C log P. Generally the partition-coefficient (P) is used in relation to un-ionized compounds while the distribution-coefficient (D) is used in relation to all species of the compound and is pH dependent.

In pharmaceutics, the two phases in measuring P are commonly water and 1-octanol and the resulting partition value is expressed as the log P according to the formula:

$$Log P_{oct/wat} = \frac{[C_u]_o}{[C_u]_w}$$

where $[C_u]_o$ and $[C_u]_w$ are the concentrations of an unionized species u in octanol (o) and aqueous phases (w)

The log P provides a measure of the hydrophilic ("water-loving") or hydrophobic ("water-fearing") nature of the compound. Hydrophobic drugs have a high octanol/water partition coefficients while hydrophilic drugs have low octanol/water partition coefficients. For example the hydrophilic molecule ascorbic acid has a log $P_{o/w}$ of −1.85 while the highly lipophilic drug clotrimazole has a log $P_{o/w}$ of 5.2. The range of experimentally determined log P values in common drugs is about −2.0 to ~5.2. See Avdeef, A. Absorption and Drug Development: Solubility, Permeability and Charge state. John Wiley and Sons 2003, Table 4.1, pgs. 59-66.

In certain embodiments where the hydrophobicity of the drug molecules is not high enough to match a given QD, the drug and QD solutions can be first mixed and the formed binary solvent (e.g., $H_2O$/tetrahydrofuran (THF)) removed by evaporation. The final residue is then reconstituted in a suitable buffer (e.g. deionized water (DI) or phosphate-buffered saline (PBS)). This process (often called solid dispersion) is able to force drug molecule impregnation. Excess unbound drug molecules can be removed by ultrafiltration or dialysis.

The isolated QD-DDS can be used as stimuli-responsive drug carriers that can release the drug molecules upon irradiation with an excitation light. The mechanisms by which the excited QD particles release the drug molecule may include one or more of increased ligand vibration, altered surface polarization, and increased water molecules agitation in the interfacial sites.

The pharmaceutical compositions including drug loaded QD disclosed herein are adapted for enteral administration in certain embodiments. In other embodiments the pharmaceutical compositions are adapted to be administered parenterally, i.e., intraarterially, intravenously, intraperitoneally, intrathecally, subcutaneously, or intramuscularly. In certain embodiments, the pharmaceutical compositions are administered intravenously or intraperitoneally by a bolus injection.

In other delivery embodiments, the pharmaceutical preparations including drug loaded QD disclosed herein are contacted with target tissue by direct application of the preparation to the tissue. The application may be made topically or by "open" or "closed" procedures. As used herein "topical" means direct application of the preparation to a tissue exposed to the environment, such as but not limited to the skin or mucous membranes and the external auditory canal. "Open procedures" means those procedures that involve cutting through the skin, mucous membranes or other tissue of a patient to expose and directly visualize the underlying tissue for application of the preparation. This may be accomplished surgically, including via a thoracotomy for lung access, abdominal laparotomy abdominal viscera access, or other direct surgical approach to the target tissue. "Closed procedures" are percutaneous endoscopic procedures in which internal target tissues are not directly visualized, but accessed and visualized via instruments inserted through small openings in the skin or mucous membrane. For example, the laparoscopy is a closed procedure performed on the abdomen while arthroscopy is a closed procedure performed to access and treat a joint. Posterior chamber intraocular surgery may be performed using closed procedures. The preparations may be administered through the endoscopic devices.

Pharmaceutical compositions comprising drug loaded QD drug may further include standard excipients including water, buffered water, tonicity adjusting agents including for example sodium acetate, sodium lactate, sodium chloride, potassium chloride, calcium chloride, and the like, and pH adjusting agents. Further agents for enhanced stability, such as albumin, lipoprotein, globulin, glycine, dextrose and the like may be included. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration.

A hydrophobic drug molecule adsorbed onto a water soluble QD as described in examples herein will form a drug delivery system that is stable, e.g. can be centrifuged, evaporated, shipped, and reformulated.

After administration and accumulation in target tissue if desired, the drug molecule is released upon light irradiation. One possible mechanism for this is release that excitation induces vibrational modes, agitating ligands bound to the QD such that they release the drug molecule. High intensity irradiation may also cause caused warming (40-45° C.), which may increase the vibrations. Light irradiation within a human can occur by apposition of a light emitter in sufficient proximity to the deposited drug to induce release. The light emitter can be placed in proximity to any target tissue including skin, mucous membranes, intra-ocular tissues and internal tissues either directly where tissue penetration permits sufficient light transmission or through open or closed procedures.

EXAMPLE 4

Light Responsive Drug Delivery System Including Targeting Ligands

In certain embodiments, the water soluble QD is modified to include targeting ligands that are added to the QD prior to drug loading. Thus, in one embodiment quantum dot nanoparticles are synthesized that are non-toxic and water soluble (biocompatible) and are surface equipped with a conjugation capable function (COOH, OH, $NH_2$, SH, azide, alkyne). By virtue of the functional groups that can be added to the QD, such as for example the COOH functional group provided in Example 2 herein, the QD can be modified to include a targeting ligand that allows the QD to selectively adhere to targeted tissue and accumulated in target tissue. The targeting ligand modified QD is loaded with a drug and delivered. The drug is released locally by light excitation.

In one exemplified embodiment, the water soluble non-toxic QD is or becomes carboxyl functionalized. The COOH-QD is linked to the amine terminus of a tumor targeting antibody using a chemical method such as for example a carbodiimide linking technology employing water-soluble 1-ethyl-3-(-3-dimethylaminopropyl) carbodiimide hydrochloride (EDC). The carboxyl functionalized QD is mixed with EDC to form an active O-acylisourea intermediate that is then displaced by nucleophilic attack from primary amino groups on the monoclonal antibody in the reaction mixture. If desired, a sulfo derivative of N-hydroxysuccinimide (sulfo-NHS) is added during the reaction with the primary amine bearing antibody. With the sulfo-NHS addition, the EDC couples NHS to carboxyls, forming an NHS ester that is more stable than the O-acylisourea intermediate while allowing for efficient conjugation to primary amines at physiologic pH. In either event, the result is a covalent bond between the QD and the antibody. Other chemistries like Suzuki-Miyaura cross-coupling, succinimidyl 4-(N-maleimidomethyl) cyclohexane-1-carboxylate (SMCC), or aldehyde based reactions may alternatively be used.

In one embodiment, non-toxic water soluble QDs are chemically attached to an antibody directed to the extracellular domain of a molecule that is preferentially expressed on tumor tissues or is required for tumor growth. There are a number of examples of such molecules against which monoclonal antibodies have been developed including carcinoembryonic antigen (CEA), epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumour necrosis factor (TNF)-related apoptosis-inducing ligand receptor 1 (TRAILR1; also known as TNFRSF10A), TRAILR2 (also known as TNFRSF10B), receptor activator of nuclear factor-KB ligand (RANKL; also known as TNFSF11), VEGF receptor (VEGFR), integrin $\alpha V\beta 3$, integrin $\alpha 5\beta 1$, fibroblast activation protein (FAP), tenascin, CD20, CD30, CD33, CD52, EpCAM, gpA33, Mucins, TAG-72, carbonic anhydrase IX (CAIX), PSMA, folate-binding protein, gangliosides GD2, GD3, and GM2, Programmed Cell Death 1 Ligand 2 (PD-L2), and telemerase subunits.

Conjugation of a water soluble non-toxic QD to a monoclonal antibody to the ERBB2 target, trastuzumab (marketed under the tradename Herceptin®), is exemplified. Herceptin® is used in the treatment of HER2, a.k.a. ERBB2, positive breast cancer and gastric or gastro-esophageal cancer.

Covalent Conjugation of In Vivo Compatible Water Dispersible Cadmium Free QD with Trastuzumab:

In Eppendorf tubes, 1 mg carboxyl-functionalised, water-soluble QDs were mixed with 100 µl MES activation buffer (i.e. 25 µl of 40 mg/ml stock into 100 µl MES). The MES buffer was prepared as a 25 mM solution (2-(N-morpholino) ethanesulfonic acid hemisodium salt (MES), Sigma Aldrich) in deionized (DI) water, pH 4.5. To this was added 33 µl of a fresh EDC solution (30 mg/ml stock in DI water, 1-ethyl-3-(3-dimethylaminopropyl) carbodiimide hydrochloride (EDC), Fisher Scientific) and the solution was mixed. To this was added 4 µl of fresh sulfo-NHS (100 mg/ml stock, ThermoFisher Scientific, in DI water) and the solution was mixed. NanoSep 300K filters (PALL NanoSep 300K Omega ultrafilters) were pre-wetted in 100 MES. The MES/EDC/Sulfo-NHS/QD solution was added to the NanoSep 300K filter and topped up 500 µl with MES. The filter was centrifuged at 5000 rpm/15 min. The retained dots were re-dispersed in 50 µl activation buffer and transferred to an Eppendorf tube containing 10 µl of trastuzumab (Herceptin®, 100 mg/ml stock in a 25 mM solution of HEPES buffer, pH 8.5)+40 µl HEPES, pH 8.5. The solution was mixed well and incubated at RT overnight (around 16-18 hours). The solution was quenched with 16 µl of 6-amino caproic acid (6AC) (19.7 mg/100 mM). Note that quenching could be alternatively conducted with other compounds having a primary amine, but 6AC was selected for this embodiment because it has a COOH and can maintain the colloidal stability of the product. The solution was transferred to a pre-whetted Nanosep 300K filter (100 µl 1×PBS) and topped-up to the 500 µl line with 1×PBS. Excess SAV was removed by three cycles of ultrafiltration using Nanosep 300K filters and 1×PBS buffer. Each cycle of centrifugation was 5000 rpm for 20 min with re-dispersal with ~400 ul of 1×PBS after each cycle. The final concentrated was re-dispersed in 100 µl PBS. The prepared traztuzumab conjugated QD were shown to fluoresce brightly and to bind to the surface of HER2 positive 4T1 cells without binding to control HER2 negative 4T1 cells.

EXAMPLE 5

Preparation of Azulene QD-DDS

In one test embodiment, drug loading was tested using the visually observable organic compound azulene. Azulene, also known by its systematic IUPAC name as bicyclo[5.3.0] decapentaene, is an isomer of naphthalene. Azulene is a solid crystalline material that is essentially insoluble in water (solubility=0.02 g/100 g of water). The log $P_{oct/wat}$ of azulene is 2.79. Azulene is soluble in organic solvents. The structure of azulene is shown below:

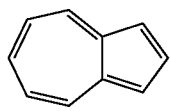

About 50 mg of 633 nm emissive water soluble QDs (Vivodots™ nanoparticles offered by Nanoco Technologies Limited) were dispersed in 610 µL of H₂O. To this solution 0.5 mg azulene in 50 µL propylene glycol was added drop wise while mixing.

Figure 3:
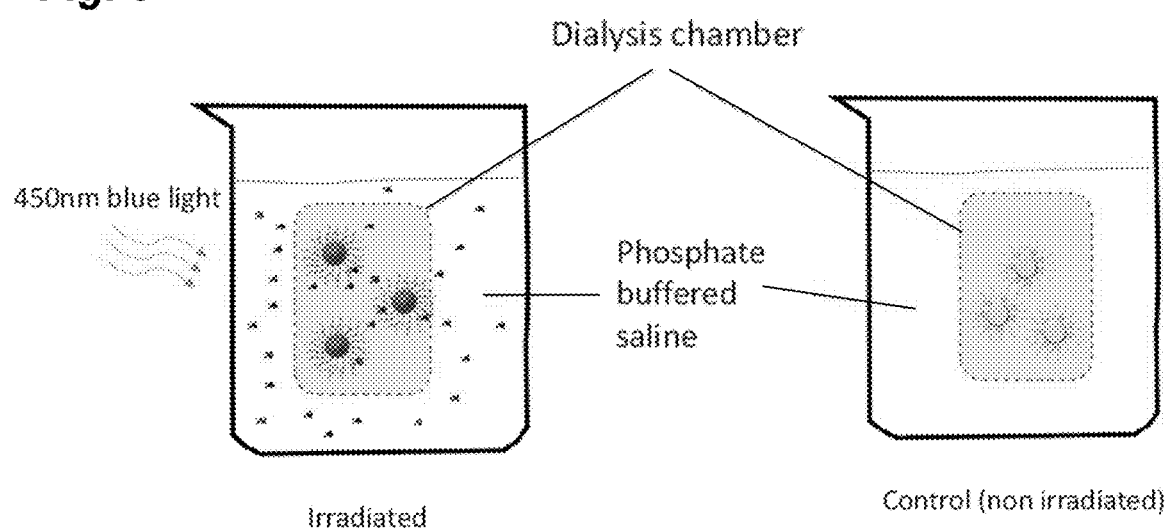
FIG. 3 depicts an exemplary experimental set-up for testing light induced drug release from drug loaded quantum dots.
Figure 4:
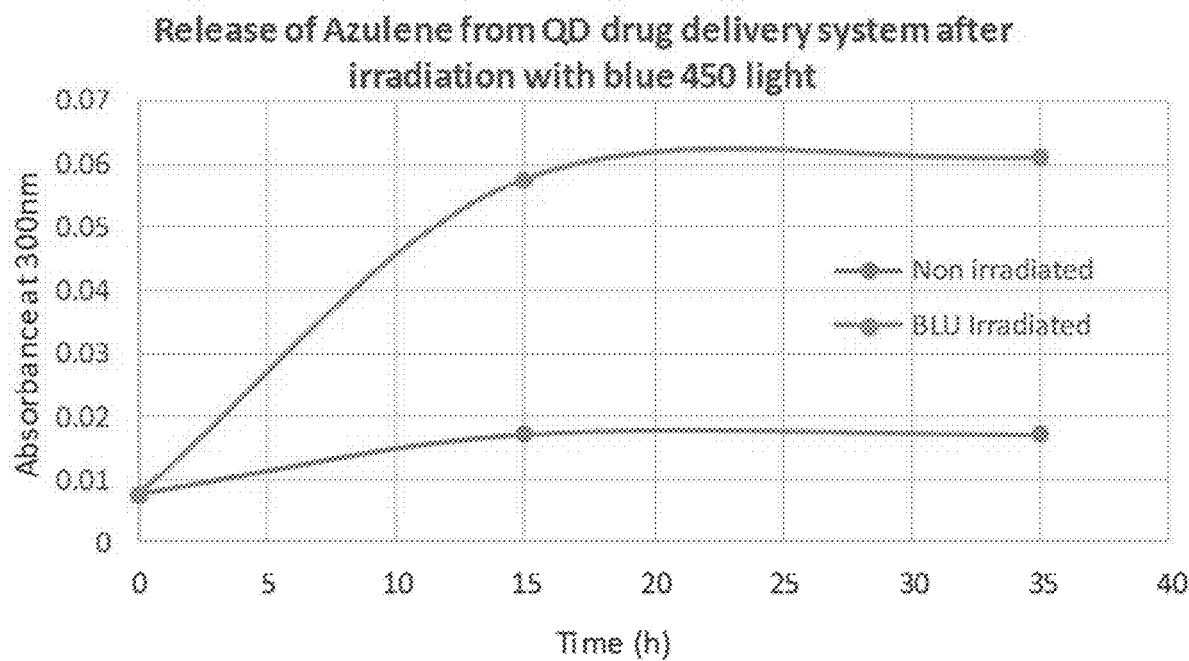
FIG. 4 shows experimental results of release of azulene from a quantum dot drug delivery system after irradiation with blue 450 nm light.

The blue azulene drops went straight into the QD solution and the final solution did not show any blue precipitate despite the fact that azulene is insoluble in water. The color of the final solution turned brown but was strongly fluorescent when excited. To test the light responsiveness of the formed Azulene QD-DDS, two 250 mL glass beakers were filled each with 200 mL of PBS+0.1% Tween 80 solution. Then 0.5 mL of QD-DDS solution (each 20 mg) were injected into a Slide-A-Lyzer™ dialysis cassette (25 kDa cutoff, Thermo Fisher Scientific Inc). Two cassettes were prepared and immersed one in each beaker. One of the beakers was irradiated with a weak 450 nm light from a BLU (Back Light Unit, light power: 2.5 mw/cm²) panel, the other was left in the dark (FIG. 3). Samples of solutions were removed from the beakers at predetermined intervals and the UV spectra were taken using a UV Cary spectrometer. As shown in FIG. 4, the irradiated beaker showed significant release of azulene whereas the non-irradiated beaker showed a small baseline release.

EXAMPLE 6

Preparation of 7-Ethyl-10-hydroxycamptothecin QD-DDS

To test drug loading and release, the drug 7-ethyl-10-hydroxycamptothecin was tested. The CAS number for 7-ethyl-10-hydroxycamptothecin is 86639-52-3 and it is also known as SN-38. 7-Ethyl-10-hydroxycamptothecin is an anti-neoplastic drug formed as an active metabolite of irinotecan but has 1000 times more activity than irinotecan. Irinotecan is derived from the natural compound camptothecin and functions as a topoisomerase I inhibitor. Irinotecan is sold under the brand name Camptosar®, among others. Topotecan, marketed by GlaxoSmithKline under the tradename trade name Hycamtin®) is another camptothecin analogue used in cancer treatment.

7-Ethyl-10-hydroxycamptothecin is supplied as a crystalline solid and is soluble in certain organic solvents (solubility in DMSO is 2 mg/ml) but is essentially insoluble in water. As an example of a very lipophilic molecule, the log $P_{oct/wat}$ of SN-38 is 3.36±0.5. The structure of 7-Ethyl-10-hydroxycamptothecin is shown below:

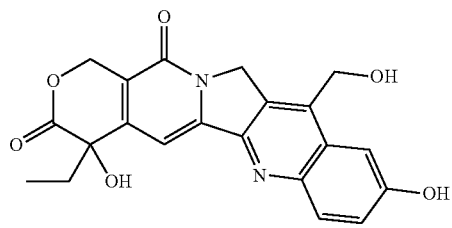 [SMILES: CCC1(O)C(=O)OCc2c1cc1n(c2=O)Cc2c-1nc1ccc(O)cc1c2CO]

The insolubility of camptothecins in water has limited their development as a clinical products. Thus efforts to solubilize camptothecins have been the subject of a number of patent applications including U.S. Pat. No. 5,447,936 (solubilizing 10-hydroxy 7-ethyl camptothecin in dimethylaceteamide and an acid), U.S. Pat. No. 5,674,874 (solubilizing 7-ethyl 10-hydroxycamptothecin in dimethyl isosorbide), U.S. Pat. No. 5,859,023 (solubilizing an A-ring substituted camptothecin in N-methyl-2-pyrrolidone), U.S.

Pat. No. 5,900,419 (solubilizing a B-ring substituted camptothecin in N-methyl-2-pyrrolidone together with an acid, PEG and a lower alcohol), among others.

In order to test loading and release of camptothecin compounds, about 38 mg of 633 nm emissive water soluble QDs (Vivodots™ nanoparticles) prepared according to Examples 1 and 2 were dispersed in 440 μL of $H_2O$. To this solution 0.5 mg 7-ethyl-10-hydroxycamptothecin in 500 μL DMSO was added drop wise while mixing. The solution remained clear with only limited cloudiness but no precipitate was observed despite the fact that 7-ethyl-10-hydroxycamptothecin is insoluble in water. To ensure full dispersion of the drug molecules to the surface of the QDs, the solution was warmed at 40° C. for a few minutes. Excess (unbound) drug molecules were removed by using ultrafiltration. This was performed by transferring the solution to Amicon 30 KDa centrifugal filtration units (Amicon Ultra-4, Millipore-Merck KGaA), diluting with DI water and then spinning at 2500 rpm for 30 min. The concentrate (~250 μL) was diluted again with 4 mL DI water and the centrifugation was repeated for a second cycle. The final concentrate (~250 μL) was diluted with 2 mL phosphate buffered saline and stored at 4° C. in the dark.

Figure 5:
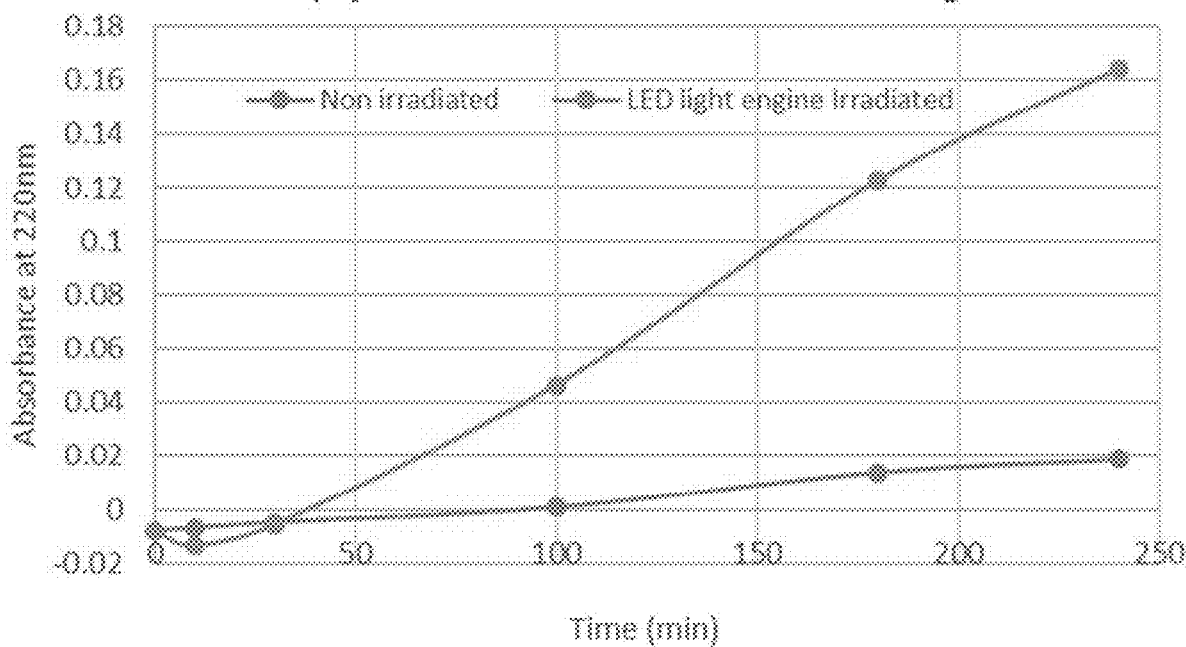
FIG. 5 shows experimental results of release of 7-ethyl-10-hydroxycamptothecin from a quantum dot drug delivery system after irradiation with blue 450 nm light.

To test the light responsiveness of the formed 7-ethyl-10-hydroxycamptothecin QD-DDS, two 250 mL glass beakers were filled each with 200 mL of PBS. Then 1 mL of QD-DDS solution (each ~15 mg) were injected into a Slide-A-Lyzer™ dialysis cassette (25 kDa cutoff, Thermo Fisher Scientific Inc). Two cassettes were prepared and one immersed in each beaker. One of the beakers was irradiated with a strong 450 nm light from an LED light engine (power: 310 $mW/cm^2$), the other was left in the dark (FIG. 3). Samples of solutions were removed from the beakers at predetermined intervals and the UV spectra were taken using a UV Cary spectrometer. As shown in FIG. 5, the irradiated beaker showed significant release of 7-Ethyl-10-hydroxycamptothecin whereas the non-irradiated beaker showed small baseline release.

EXAMPLE 7

Effect of 7-Ethyl-10-hydroxycamptothecin QD-DDS on cancer cells. The QD-DDS preparation described in Example 6 was tested on SK-BR3 human breast adenocarcinoma cells cultivated in cell culture medium (McCoy's 5A medium).

Figure 8:
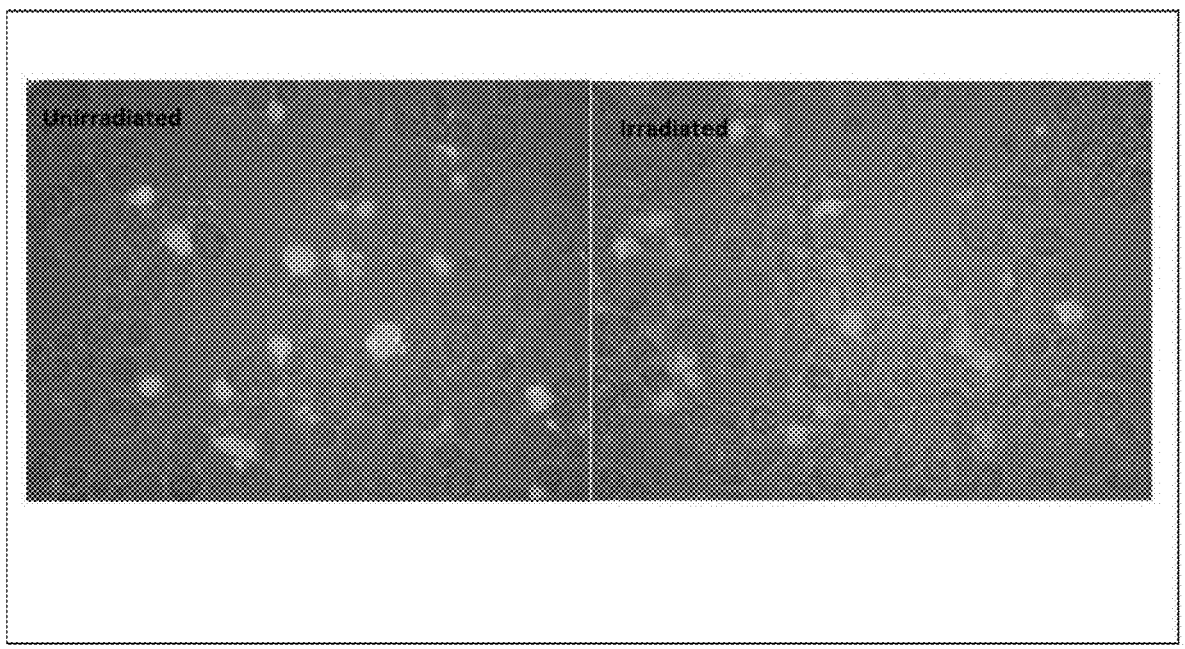
FIG. 8 depicts a microscopic view of QD-DDS-treated cancer cells before and after irradiation with green light.

Two equally cultivated dishes with about 70% cell density were treated with 7-Ethyl-10-hydroxycamptothecin QD-DDS at a final concentration of 400 micrograms/mL for 15 h, then only one of the two plates was irradiated for 5 minutes under a 2.5× objective lens of a Zeiss Axiovert200M fluorescence microscope using FITC filter set. As depicted in FIG. 8, only the irradiated plate showed significant cell damage as evidenced by the increased labelling of the cells due to the compromised integrity of cellular membrane.

EXAMPLE 8

Water Soluble Surface Modified QDs

In one embodiment, a method of generating and using water soluble QDs is provided using mercapto based polar ligands to render the nanoparticles water soluble. Ligands such as mercapto succinic acid, mercapto undecanoic acid, mercapto hexanoic acid, mercapto propionin acid, mercapto acetic acid, cysteine, methionine, and mercapto PEG are examples but similar mercapto ligands will be apparent to those skilled in the art.

In one such method, an excess of the mercapto ligand (e.g., mercapto succinic acid) is dissolved or dispersed with sufficient amount of a common solvent for the nanoparticles and the mercapto ligand. Typical common solvents could be chloroform, DCM, THF, anisole, or toluene. Then a solution of QD in the same solvent is added and mixed vigorously for 10 to 15 minutes then left to stand for >15 hours to induce capping with the mercapto ligand. Following incubation, a few milliliters of a basic aqueous solution (e.g., ammonium hydroxide) is added and vigorously stirred for a few minutes then left stirring slowly overnight at room temperature. After this process, the QDs will be found to have migrated to the aqueous layer and may be separated such as by percolation. The aqueous QD solution is then washed repeatedly by ultrafiltration to remove excess ligands.

Figure 7:
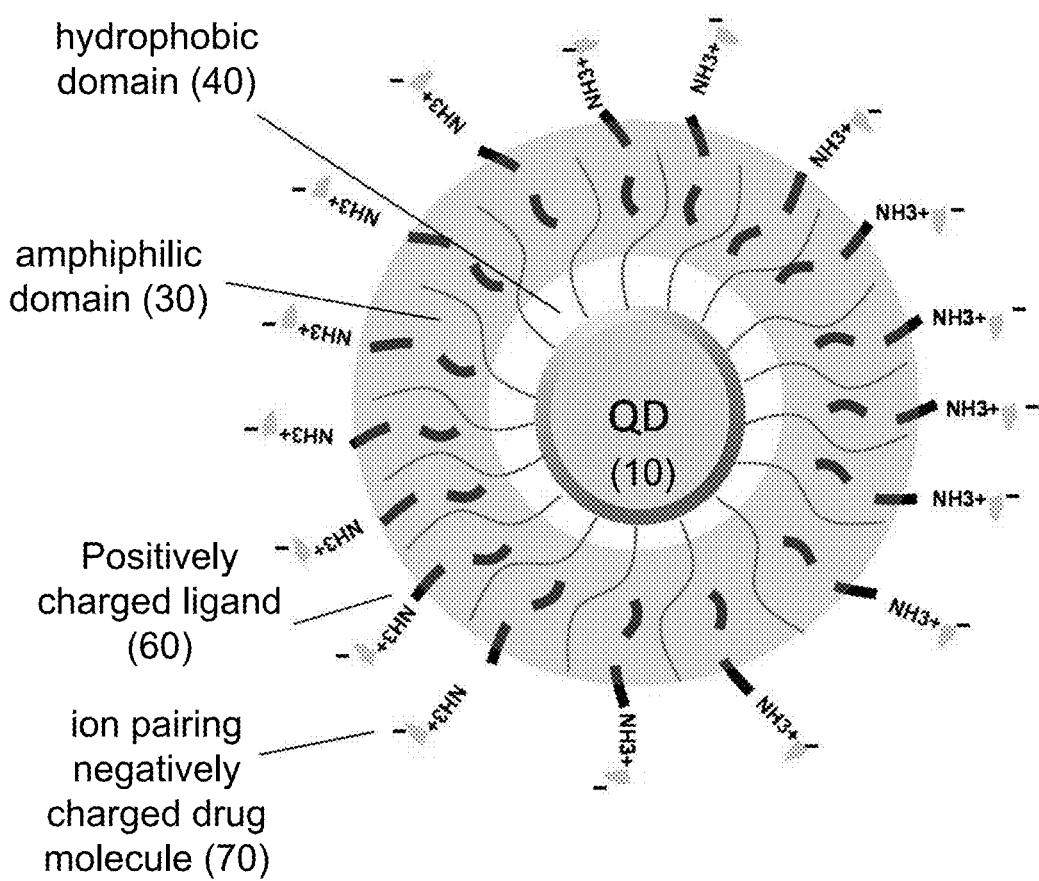
FIG. 7 provides a schematic of the incorporation and excitation-triggered release of ionic drugs from an ion pairing functionalized quantum dot.

If the QD nanoparticles in the final purified aqueous QD solutions described in Example 2 are equipped with strongly negatively charged ligands they can attract, by ion pairing, positively charged polar drug molecules like alkaloids or cationic molecules. Examples of cationic drugs include procarbazine, dacarbazine, etoposide, and amantadine. As shown figuratively in FIG. 7, if QD (10) is equipped with a strongly positively charged ligand (60) the derivitized QD can attract, by ion pairing, negatively charged (anionic) drug molecules (70) such as for example methotrexate, naproxen, indomethacin, and nucleic acids such as iRNA.

If aromatic ligands are used in the organic coating (e.g., salicylic acid) of the water soluble dots as described in Example 2, then aromatic drug molecules maybe bound to the QD by a π-π stacking effect. Examples of aromatic drugs include phenytoin (5,5-Diphenyl-imidazolidine-2,4-dione: log P of 2.47), diazepam (7-chloro-1,3-dihydro-1-methyl-5-phenyl-2H-1,4-benzodiazepin-2-one: log P of 2.82), quinazoline-containing drugs such as for example the cancer chemotherapeutic gentitinib (4-(3'-chloro-4'-Fluoroanilino)-7-methoxy-6-(3-morpholinopropoxy)quinazoline: toe of 3.2), and many others.

Figure 6:
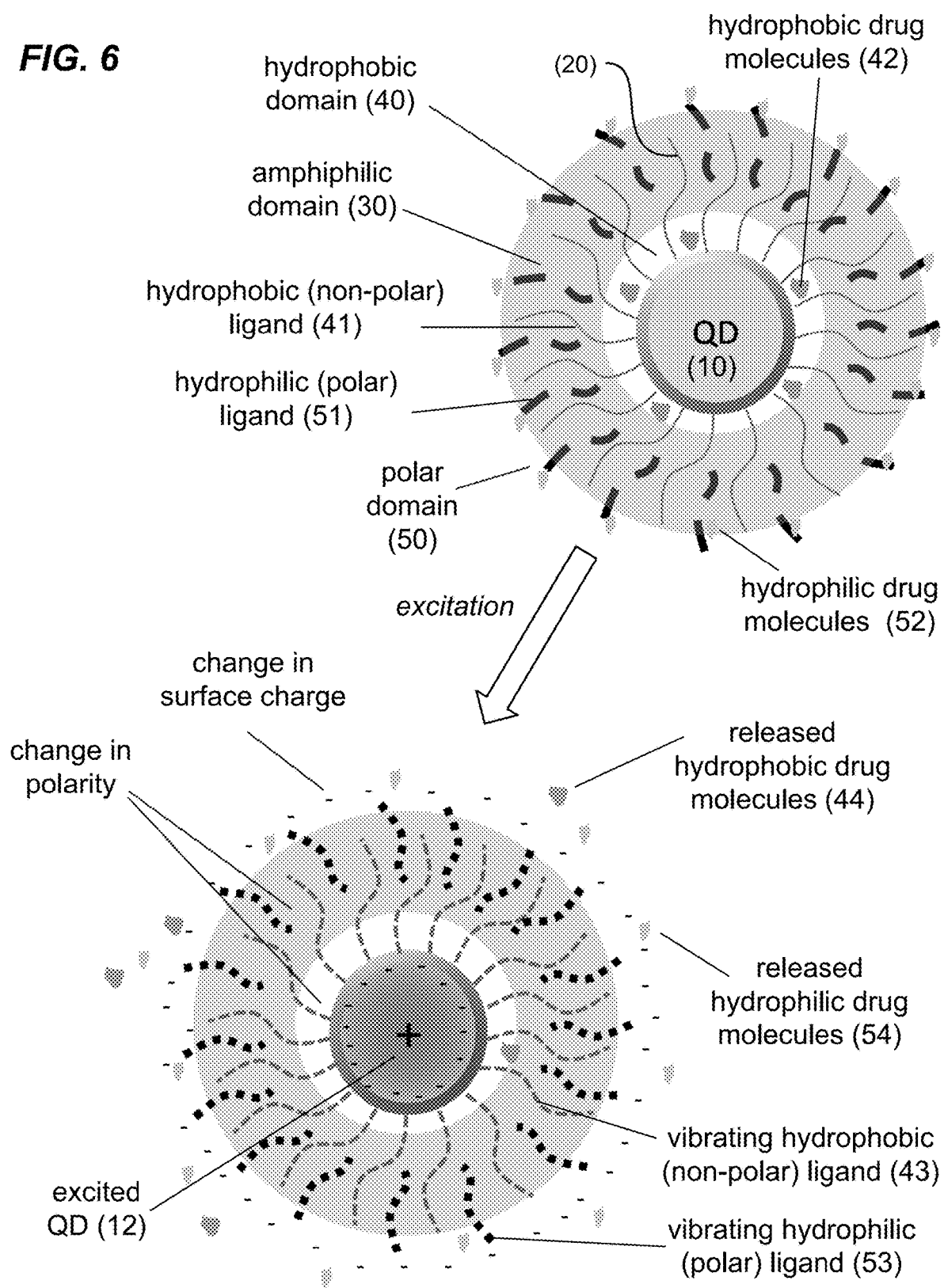
FIG. 6 provides a schematic of various modalities of drug incorporation and excitation-triggered release from different domains (hydrophobic, polar, ionic) within the structure of functionalized quantum dots.

FIG. 6 depicts a QD (10) including the alkyl chains (20) from the native capping ligands (like alkyl thiol or stearic acid). The depicted QD includes an inner hydrophobic domain (40), a middle amphiphilic domain (30) and an outer hydrophilic domain (50) and can accommodate drug loading of any of hydrophobic, amphiphilic and hydrophilic drugs with the drug entering the domain that correlates with its phobicity.

The inner hydrophobic domain (40) is generated by virtue of bound hydrophobic (non-polar) ligands (41). These non-polar ligands include the aliphatic chains from alky thiol, fatty acids, and cholesterol. The amphiphilic domain (30) may be provided by small molecules (such as guaifenesin, salicylic acid, and mercapto alkyl acids), surfactants (such as saponins and fatty acids), and polymers (such as PEG, acrylate copolymers, and polyvinyl acetate). The polar domain (50) is conferred by hydrophilic polar ligands (51) such as coating ligands selected from carboxyls, OH, $NH_2$, $NH_3^+$, and SH groups.

Where generated using largely hydrophobic cholesterol moieties according to Example 2 herein, the hydrophobicity of the inner layer (40) is conferred by the bulky steroid and hydrocarbon chains of the cholesterol. If generated using myristate the hydrocarbon tail of the myristate provides the hydrophobic environment. Whether using cholesterol or myristate as the hydrophobic moiety, the hydrophobic moiety is added by first interacting with the alkyl chains from the native ligands (by hydrophobic interaction) and then the included OH group of the hydrophobic moiety is crosslinked with other OH and COOH groups such as using a reaction with HMMM (CYMEL 303).

Examples of hydrophobic (non-ionic) drugs include steroids such as prednisolone ((11beta)-11,17,21-Trihydroxy-pregna-1,4-diene-3,20-dione: log P of 1.66), which may be loaded into the hydrophobic domain. Other non-ionic drugs including the cancer chemotherapeutic drug dactinomycin (2-amino-N,N'-bis(hexadecahydro-2,5,9-trimethyl-6,13-bis (1-methylethyl)-1,4,7,11,14-pentaoxo-1H-pyrrolo(2,1-1)(1, 4,7,10,13)oxatetra-azacyclohexadecin-10-yl)-4,6-dimethyl-3-oxo-3H-phenoxazine-1,9-dicarboxamide, a.k.a. Actinomycin D, composed of two cyclic peptides linked by a phenaxazine: log P of 1.6) may also be loaded into the hydrophobic domain (40).

Hydrophobic negatively charged drugs include retinoid acid (Tretonin, 3,7-Dimethyl-9-(2,6,6-trimethyl-1-cyclohexene-1-yl)-2,4,6,8-nonatetraenoic acid: log P of 6.3). Hydrophobic positively charged drugs include fentanyl (1-Phenethyl-4-(N-phenylpropionamido)piperidine: log P of 4.05). Hydrophobic drugs such as these may be sequestered into the inner hydrophobic domain (40) of the functionalized QD.

The hydrophilicity of certain drugs is highly charge dependent. For example the negatively charged drug warfarin (Coumadin®) has a log $D_{7.4}$ of 1.12. However, the log $P^I$ (ionized state) is 0.04 and the log $P^N$ (neutral) is 3.54. Similarly, the negatively charged non-steroidal anti-inflammatory drug sulindac (Clinoril®) has a log $D_{7.4}$ of 0.12 but a log $P^N$ (neutral) of 3.60. Hydrophilic positively charged drugs include bleomycin (C log P of −0.52), desmopressin (1-(3-mercaptopropionic acid)-8-D-arginine-vasopressin: log $P_{exp}$ of −4.2), neostigmine (3-Trimethylammoniumphenyl N,N-dimethylcarbamate: C log P of −1.6), and suxamethonium (succinylcholine: C log P of −2.5). Hydrophilic drugs such as these may be loaded into the hydrophilic domain (50) by virtue of charged groups added to the QD that interact with the drugs by charge (ionic) interactions.

One of the largest groups of drugs are the cationic amphiphilic drugs (CAD), which typically contain a hydrophobic ring structure and hydrophilic side chains with a cationic amine group. By virtue of the intervening amphiphilic domain (30) sandwiched between the inner hydrophobic domain (40) and the outer hydrophilic domain (50), the QD depicted in FIG. 6, can accommodate molecules having both hydrophilic and hydrophobic portions because the molecule can align with its hydrophobic portion in hydrophobic domain (40) and its hydrophilic portion in hydrophilic domain (50). CADs include many familiar and important drugs including: antibacterials such as gentamycin, clindamycin, telithromycin, and azithromycin; antidepressants such as fluoxetine (Prozac®) and imipramine; antiarrhythmics such as amiodarone, anti-asthmatics such as ketotifen; immunosuppressants such as sirolimus and certican; anorexic agents such as chlorphentermine; anti-seizure medications such as zonisamide; anti-psychotics such as arapiprazole and chlorpromazine; anti-Alzheimer medications such as memantine; anti-Parkinson's disease medications such as levodopa; and antihistimines such as bepotastine. Amphiphilic non-ionic drugs also include colchicine (log P of 1.85), guaifenesin (3-(2-methoxyphenoxy)propane-1,2-diol: log P of 1.39), and anastrozole (alpha,alpha, alpha',alpha'-tetramethyl-5-(1H,1,2,4-triazol-1-ylmethyl)-m-benzenediacetonitrile, aromatase inhibitor: log P of 2.4).

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

I claim:

1. A light responsive quantum dot (QD) drug delivery system (QD-DDS) comprising water soluble QD nanoparticles loaded with drug molecules, wherein the water soluble QD nanoparticles each have a hydrodynamic size of 10-20 nm and each comprise a core semiconductor material or a core/shell semiconductor material and an outer layer comprising an inner hydrophobic domain, a middle amphiphilic domain, and an outer hydrophilic domain, wherein the inner hydrophobic domain is formed from a ligand interactive agent selected from $C_{8-20}$ fatty acids, $C_{8-20}$ fatty acid esters, and cholesterol, the middle amphiphilic domain is formed from at least one surface modifying ligand crosslinked to the ligand interactive agent in a solution comprising hexamethoxymethylmelamine, and the outer hydrophilic domain is a coating ligand selected from carboxyls, OH, $NH_2$, $NH_3^+$ and SH groups, and wherein the loaded drug molecule enters the domain that correlates with phobicity of the drug molecule and is releasable from the QD-DDS upon excitation of the QD.

2. The light responsive QD-DDS of claim 1, wherein the water soluble QD nanoparticle comprises a core formed of a cadmium free semiconductor material.

3. The light responsive QD-DDS of claim 1, wherein the water soluble QD nanoparticle comprises an alloyed semiconductor material having a bandgap value that increases outwardly by graded alloying.

4. The light responsive QD-DDS of claim 1, wherein the ligand interactive agent is cholesterol.

5. The light responsive QD-DDS of claim 1, wherein the $C_{8-20}$ fatty acid ester ligand interactive agent is isopropyl myristate.

6. The light responsive QD-DDS of claim 4, wherein at least one surface modifying ligand is a monomethoxy polyethylene oxide.

7. The light responsive QD-DDS of claim 1, wherein the nanoparticles further comprise capping ligands and wherein the drug molecules are physically entrapped in the capping ligands of the nanoparticles.

8. The light responsive QD-DDS of claim 7, wherein the capping ligands are selected from the group consisting of: thiol, carboxyl, amine, phosphine, phosphine oxide, phosphonic acid, phosphinic acid, imidazole, OH, thio ether, and calixarene groups.

9. The light responsive QD-DDS of claim 1, wherein the drug molecules are hydrophobic with an octanol-water partition coefficient (log P) of greater than 0.

10. The light responsive QD-DDS of claim 1, wherein the drug molecules are hydrophobic with an octanol-water partition coefficient (log P) of greater than 1.

11. The light responsive QD-DDS of claim 1, wherein the drug molecules are released upon excitation of the QDs with an excitation source selected from a normal blue light, UV light, laser light, LED light, multiphoton excitation, and an electrical current.

12. The light responsive QD-DDS of claim 1, wherein the outer layer of the QD is derivatized with a targeting ligand prior to loading with the drug molecules.

13. The light responsive QD-DDS of claim 12, wherein the targeting ligand is a monoclonal antibody directed to a target selected from the group consisting of: carcinoembryonic antigen (CEA), epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumour necrosis factor (TNF)-related apoptosis-inducing ligand receptor 1 (TRAILR1; also known as TNFRSF10A), TRAILR2 (also known as TNFRSF10B), receptor activator of nuclear factor-κB ligand (RANKL; also known as TNFSF11), VEGF receptor (VEGFR), integrin αVβ3, integrin α5β1, fibroblast activation protein (FAP), tenascin, CD20, CD30, CD33, CD52, EpCAM, gpA33, Mucins, TAG-72, carbonic anhydrase IX (CAIX), PSMA, folate-binding protein, gangliosides GD2, GD3 and GM2, PD-L2, and telomerase subunits.

14. The light responsive QD-DDS of claim 1, wherein water soluble QD nanoparticle includes a semiconductor material selected from the group of materials consisting of ZnS, ZnSe, ZnTe, InP, InSb, AlP, AlS, AlSb, GaN, GaP, GaSb, PbS, PbSe, AgInS$_2$, AgS, CuInS$_2$, Si, Ge and alloys and doped derivatives thereof.

15. The light responsive QD-DDS of claim 1, wherein the water soluble QD includes a heavy metal semiconductor material selected from the group consisting of cadmium (Cd), lead (Pb), mercury (Hg), vanadium (V) and arsenic (As) and alloys and doped derivatives thereof.

16. A method of treating a target tissue comprising administering the drug loaded light responsive QD-DDS according to claim 1 and administering light to the target tissue sufficient to excite the QD and induce release of the drug from the QD-DDS.

17. The method of claim 16, wherein the drug loaded light responsive QD-DDS is used to diagnose, treat, cure, mitigate, or prevent disease states of humans, animals, plants, and other organisms.

18. The method of claim 16, wherein the drug loaded light responsive QD-DDS is administered systemically by a route selected from intraarterial, intravenous, intraperitoneal, intrathecal, subcutaneous, intramuscular, intratumoral, oral, sublingual, nasal, rectal, epidural and pulmonary routes.

19. The method of claim 16, wherein the drug loaded light responsive QD-DDS is administered during a surgical operation by direct instillation or spraying a target tissue.

20. The light responsive QD-DDS of claim 1 wherein the drug is a camptothecin.

21. The light responsive QD-DDS of claim 20 wherein the camptothecin is 7-Ethyl-10-hydroxycamptothecin.

22. The light responsive QD-DDS of claim 1 wherein the amphiphilic domain comprises salicylic acid and the drug molecule is an aromatic drug selected from the group consisting of phenytoin, diazepam, and quinazoline containing drugs.

23. The light responsive QD-DDS of claim 1 wherein the drug is a hydrophobic drug selected from prednisolone, Actinomycin D, retinoic acid, and fentanyl.

24. The light responsive QD-DDS of claim 1 wherein the drug is a hydrophilic drug selected from bleomycin, desmopressin, neostigmine, and suxamethonium.

25. The light responsive QD-DDS of claim 1 wherein the drug is an amphiphilic drug selected from gentamycin, clindamycin, telithromycin, azithromycin, fluoxetine, imipramine; amiodarone, ketotifen, sirolimus, certican, chlorphentermine, zonisamide, aripiprazole, chlorpromazine, memantine, levodopa, bepotastine, colchicine, guaifenesin, and anastrozole.

\* \* \* \* \*